(12) United States Patent
Giffen et al.

(10) Patent No.: US 10,297,143 B1
(45) Date of Patent: May 21, 2019

(54) DETECTING QUALITY OF PHYSIOLOGIC DATA USING CONTACT PRESSURE DATA FOR ALARM GENERATION

(71) Applicant: International Business Machines Corporation, Armonk, NY (US)

(72) Inventors: Perry R. Giffen, Kemptville (CA); James R. Green, Ottawa (CA); Shermeen Nizami, Ottawa (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/927,844

(22) Filed: Mar. 21, 2018

(51) Int. Cl.
    G08B 29/18 (2006.01)
    G08B 21/02 (2006.01)

(52) U.S. Cl.
    CPC ........... G08B 29/185 (2013.01); G08B 21/02 (2013.01)

(58) Field of Classification Search
    CPC ...... G08B 29/185; G08B 21/02; G08B 21/04; G08B 21/0407; G08B 21/0423; G08B 21/0438; G08B 21/0446; G08B 21/0453; G08B 21/0461; G08B 29/18; G08B 29/188; A61B 5/00; A61B 5/0823; A61B 5/0826; A61B 5/103; A61B 5/1036; A61B 5/11; A61B 5/1116; A61B 5/113; A61B 5/4561; A63B 23/0244
    See application file for complete search history.

(56) References Cited

U.S. PATENT DOCUMENTS 8,979,765 B2    3/2015  Banet et al.
9,039,730 B1 *  5/2015  McEwen ............ A61B 17/135
                                               600/490
(Continued)

FOREIGN PATENT DOCUMENTS

WO    9322624 A1    11/1993

OTHER PUBLICATIONS

Bitan, Y. and M.F. O'Connor, "Correlating Data from Different Sensors to Increase the Positive Predictive Value of Alarms: an Empiric Assessment", Copyright : © 2012, Version 1. F1000Res. 2012, Published online Nov. 8, 2012. doi: 10.12688/f1000research. 1-45.v1, Total 8 pp.

(Continued)

*Primary Examiner* — Brian Wilson
(74) *Attorney, Agent, or Firm* — Konrad Raynes Davda & Victor LLP; Janaki K. Davda (57) ABSTRACT

Provided are techniques for detecting quality of physiologic data using contact pressure data for alarm generation. First data is received that comprises physiologic data and an alarm condition. Second data is received from pressure-sensitive sensors, wherein the second data comprises contact pressure data. In response to determining that the second data indicates movement of an entity, a delay is created for generation of an alarm for the alarm condition. In response to determining that the delay has expired, it is determined whether the first data has changed to indicate that the alarm condition is resolved. In response to determining that the first data has changed to indicate that the alarm condition is resolved, the alarm condition is cleared. In response to determining that the first data has not changed to indicate that the alarm condition is resolved, the alarm is generated.

18 Claims, 8 Drawing Sheets

(56) References Cited

U.S. PATENT DOCUMENTS

| | | | | |
|---|---|---|---|---|
| 2011/0112442 | A1* | 5/2011 | Meger | A61B 5/0002 600/595 |
| 2011/0245688 | A1* | 10/2011 | Arora | A61B 5/0205 600/483 |
| 2016/0213537 | A1* | 7/2016 | Hayes | G06Q 50/22 |
| 2017/0325683 | A1 | 11/2017 | Larson et al. | |

OTHER PUBLICATIONS

Graham, K.C. and M. Cvach, "Monitor Alarm Fatigue: Standardizing Use of Physiological Monitors and Decreasing Nuisance Alarms", © 2010 American Association of Critical-Care Nurses doi: 10.4037/ajcc2010651, Downloaded from http://ajcc.aacnjournals.org/ by AACN on Nov. 28, 2017, Total 11 pp.

Kilinc, D. and M. Ghattas, "Implementing an Intelligent Alarm System in Intensive Care Units", Degree Project in Medical Engineering, Stockholm, Sweden 2016, Total 135 pp.

Mell, P. and T. Grance, "Effectively and Securely Using the Cloud Computing Paradigm", [online], Oct. 7, 2009 retrieved from the Internet at <URL: http://csrc.nist.gov/groups/SNS/cloud-computing/cloud-computing-v26.ppt>, Total 80 pp.

Mell, P. and T. Grance, "The NIST Definition of Cloud Computing (Draft)", Sep. 2011, Computer Security Division Information Technology Laboratory National Institute of Standards and Technology, Total 7 pp.

Nizami, S., J.R. Green, and C. McGregor, "Implementation of Artifact Detection in Critical Care: A Methodological Review", IEEE Reviews in Biomedical Engineering, vol. 6, 2013, Date of publication Jan. 30, 2013; date of current version Mar. 29, 2013, Total 16 pp.

Vergales, B.D., A.O. Paget-Brown, H. Lee, L.E. Guin, T.J. Smoot, C.G. Rusin, M.T. Clark, J.B. Delos, K.D. Fairchild, D.E. Lake, R. Moorman, and J. Kattwinkel, "Accurate Automated Apnea Analysis in Preterm Infants", Published online Apr. 16, 2013. doi: 10.1055/s-0033-1343769, Total 8 pp.

* cited by examiner

DETECTING QUALITY OF PHYSIOLOGIC DATA USING CONTACT PRESSURE DATA FOR ALARM GENERATION

FIELD

Embodiments of the invention relate to detecting quality of physiologic data using contact pressure data for alarm generation. In particular, embodiments relate to reducing false alarms in physiologic monitors through sensor fusion between physiologic sensors and pressure-sensitive sensors.

BACKGROUND

In some situations, such as when a patient is in a hospital (e.g., in a Neonatal Intensive Care Unit (NICU)), there is physiologic monitoring of the patient (e.g., monitoring of heart rate and blood oxygen saturation ($SpO_2$)). When physiologic data reaches certain thresholds, a physiologic monitor alarm may be set off so that a nurse or doctor can check on the patient. A false alarm may be described as an alarm that is set off even though the patient does not need to be checked on and, as such, the alarm has no clinical significance.

False alarms cause noise and alarm fatigue for those monitoring the physiologic data and desensitize clinicians to patient alarms. For example, alarm fatigue may result in staff desensitization and a decrease in quality of monitoring (e.g., ignoring of true (not false) alarms).

SUMMARY

In accordance with embodiments, a computer-implemented method is provided for detecting quality of physiologic data using contact pressure data for alarm generation.

The computer-implemented method comprises: receiving first data that comprises physiologic data and an alarm condition; receiving second data from pressure-sensitive sensors, wherein the second data comprises contact pressure data; in response to determining that the second data indicates movement of an entity, creating a delay for generation of an alarm for the alarm condition; in response to determining that the delay has expired, determining whether the first data has changed to indicate that the alarm condition is resolved; in response to determining that the first data has changed to indicate that the alarm condition is resolved, clearing the alarm condition; and, in response to determining that the first data has not changed to indicate that the alarm condition is resolved, generating the alarm.

In accordance with other embodiments, a computer program product is provided for detecting quality of physiologic data using contact pressure data for alarm generation. The computer program product comprising a computer readable storage medium having program code embodied therewith, the program code executable by at least one processor to perform operations comprising: receiving first data that comprises physiologic data and an alarm condition; receiving second data from pressure-sensitive sensors, wherein the second data comprises contact pressure data; in response to determining that the second data indicates movement of an entity, creating a delay for generation of an alarm for the alarm condition; in response to determining that the delay has expired, determining whether the first data has changed to indicate that the alarm condition is resolved; in response to determining that the first data has changed to indicate that the alarm condition is resolved, clearing the alarm condition; and, in response to determining that the first data has not changed to indicate that the alarm condition is resolved, generating the alarm.

In yet other embodiments, a computer system is provided for detecting quality of physiologic data using contact pressure data for alarm generation. The computer system comprises one or more processors, one or more computer-readable memories and one or more computer-readable, tangible storage devices; and program instructions, stored on at least one of the one or more computer-readable, tangible storage devices for execution by at least one of the one or more processors via at least one of the one or more memories, to perform operations comprising: receiving first data that comprises physiologic data and an alarm condition; receiving second data from pressure-sensitive sensors, wherein the second data comprises contact pressure data; in response to determining that the second data indicates movement of an entity, creating a delay for generation of an alarm for the alarm condition; in response to determining that the delay has expired, determining whether the first data has changed to indicate that the alarm condition is resolved; in response to determining that the first data has changed to indicate that the alarm condition is resolved, clearing the alarm condition; and, in response to determining that the first data has not changed to indicate that the alarm condition is resolved, generating the alarm.

BRIEF DESCRIPTION OF THE SEVERAL VIEWS OF THE DRAWINGS

Referring now to the drawings in which like reference numbers represent corresponding parts throughout.

DETAILED DESCRIPTION

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Figure 1:
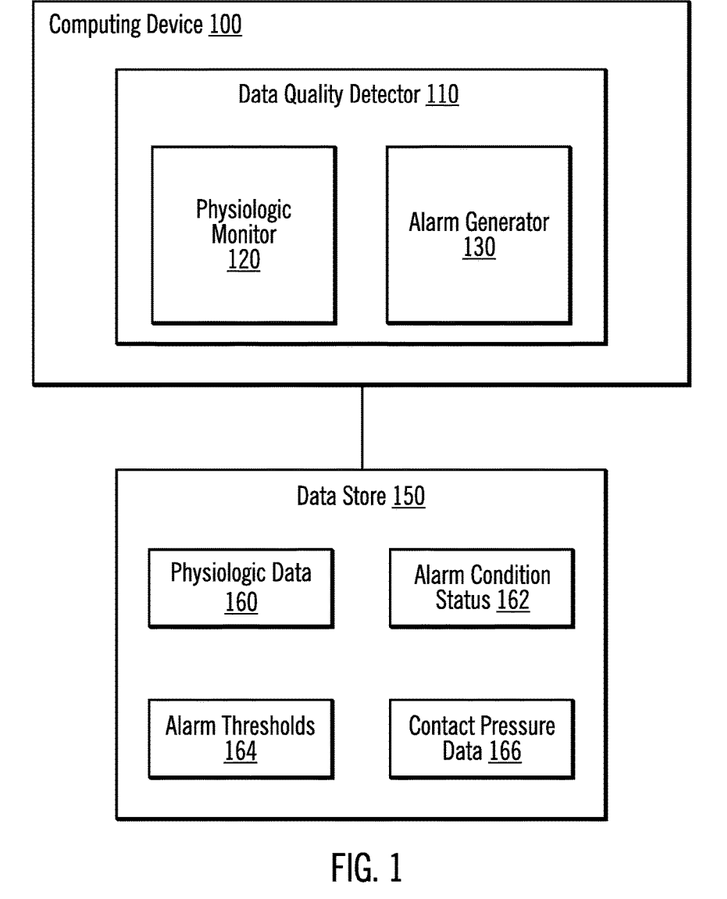
FIG. 1 illustrates, in a block diagram, a computing environment in accordance with certain embodiments.

FIG. 1 illustrates, in a block diagram, a computing environment in accordance with certain embodiments. A computing device 100 includes a data quality detector 110. The data quality detector 110 includes a physiologic monitor 120 and an alarm generator 130. The physiologic monitor 120 may be referred to as a patient monitor or as a physiologic patient monitor. The computing device 100 includes or is coupled to data store 150. The data store 150 includes physiologic data 160, alarm condition status 162 (i.e., physiologic alarm data), alarm thresholds 164, and contact pressure data 166 (also referred to as pressure-sensitive data). The contact pressure data 166 serves as the source for extracting information about secondary data, including motion and other relevant signals. With embodiments, there may be different alarm thresholds 164 for different types and severity of alarms.

With embodiments, the pressure-sensitive sensors measure contact pressure using a grid of sensors. The pressure-sensitive sensors produce contact pressure data over time that may be collectively visualized in the form of an image and video. The pressure-sensitive data is used for continuous monitoring of adults and children, in the hospital and at home, as well as in clinical and other environments.

Pressure-sensitive sensors may be incorporated into mattresses or into mats that are placed on top of mattresses and covered by a blanket to avoid direct contact with a patient.

The contact pressure data may be used to assess patient mobility, automotive seating comfort, bed occupancy, fluid redistribution through the body (e.g., with respect to congestive heart failure), pressure ulcers, respiration rate estimation, and sleep apnea detection. Pressure-sensitive sensors can generate indicators for nurses when it is time for repositioning the patient.

For example, patient movement impacts the integrity of physiologic data captured by the physiologic monitor 120. Artifacts due to patient movement and other non-physiologic conditions cause true, but brief, breaches of alarm limits, without clinical significance. Embodiments provide continuous motion detection using the contact pressure data from the pressure-sensitive sensors. Then, embodiments combine the information from the contact pressure data with the physiologic data to determine whether to issue an alarm.

With embodiments, the physiologic sensors that are used to monitor the patient are attached to the patient. For example, electrocardiograph (ECG) electrodes may be placed on the patient's chest or a blood oxygen saturation ($SpO_2$) pulse oximeter sensor may be attached to the patient's limb (e.g., finger).

In particular, motion artifacts arising from patient movement is a source of interference in physiologic data streams, such as blood oxygen saturation (SpO2) measured by pulse oximeters. Patient movement may be self-initiated or externally-induced, such as that caused by routine care or clinical interventions. Such motion artifacts cause physiologic monitors to trigger clinically irrelevant, false alarms. Artifacts may be described as components of a signal arising from unintended sources other than the physiologic system that is being measured.

Figure 2:
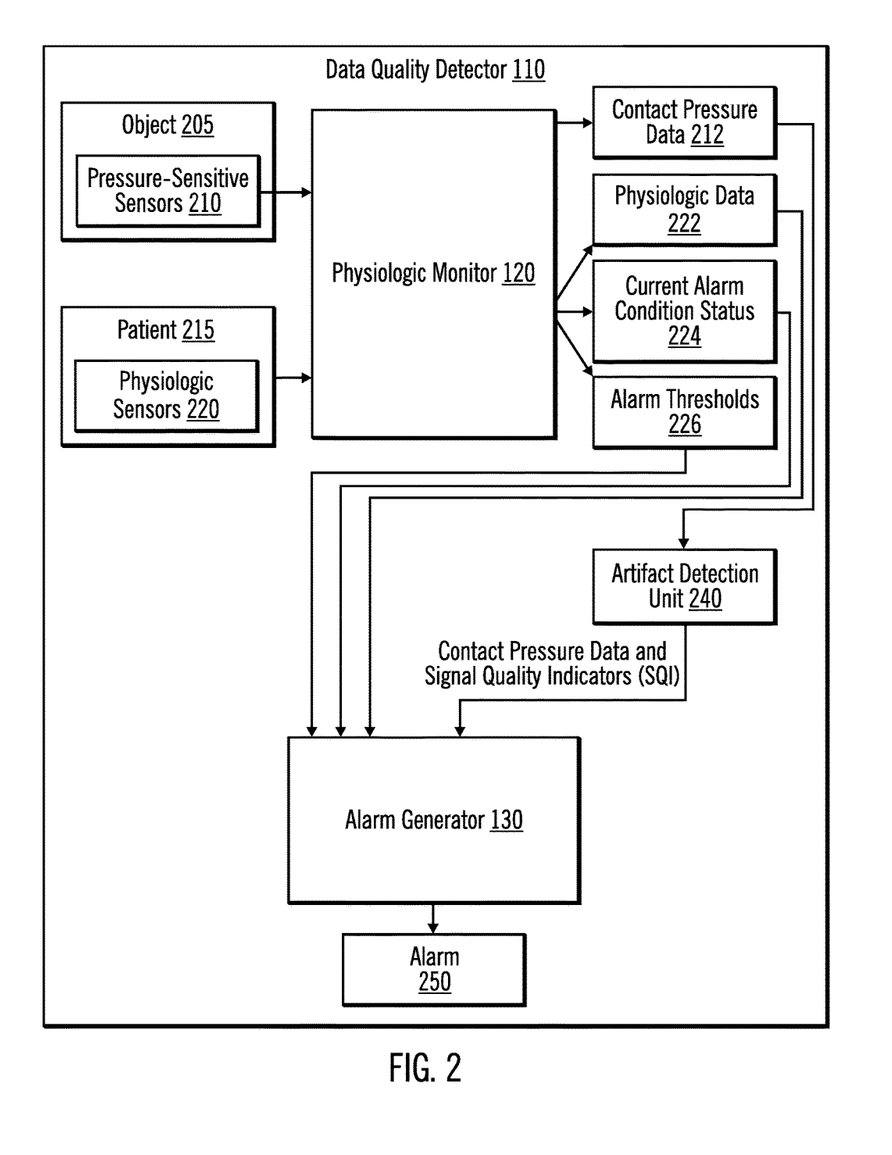
FIG. 2 illustrates, in a block diagram, further details of a data quality detector in accordance with certain embodiments.

FIG. 2 illustrates, in a block diagram, further details of a data quality detector 110 in accordance with certain embodiments. The physiologic monitor 120 collects input data (contract pressure data 212) from pressure-sensitive sensors 210 coupled to an object 205. The physiologic monitor 120 also collects input data (physiologic data 222) from physiologic sensors 220 coupled to a patient 215. With embodiments, a photoplethysmograph is used for SpO2 estimation. With embodiments, the object 205 may be a mat, a wearable item (e.g., a shirt, jacket, sweater, pants, etc.), a mattress, a bedsheet, a fabric, or similar embodiments; and the pressure-sensitive sensors are embedded in the object 205.

The physiologic monitor 120 outputs the contact pressure data 212 from the pressure-sensitive sensors 210 to an artifact detection unit 240. The physiologic monitor 120 outputs the physiologic data 222, the current alarm condition status 224 for each alarm, and alarm thresholds 226 for each alarm to an alarm generator 130. With embodiments, each alarm has a lower alarm threshold and an upper alarm threshold. With embodiments, the alarm thresholds 226 are static and set within the physiologic monitor 120. With embodiments, based on the alarm thresholds 226, the current alarm condition status 224 is generated by the physiologic monitor 120.

The physiologic data 222 may include multiple physiologic data streams. The current alarm condition status 224 includes an alarm condition status for each of the physiologic data streams. An alarm condition status indicates whether an alarm has been triggered for the corresponding physiologic data stream. With embodiments, the physiologic data 222 and current alarm condition status 224 represent different data streams (e.g., a data stream for physiologic data of blood oxygen saturation ($SpO_2$) and a data stream for the current alarm condition status for an $SpO_2$ alarm). The artifact detection unit 240 detects artifacts, for example motion artifacts caused by patient movement, to generate Signal Quality Indicators (SQI) and outputs the contact pressure data 212 and the corresponding signal quality indicators. With embodiments, a signal quality indicator may be described as a variable (number or string) that reflects the quality of a signal. A signal quality indicator may be binary, continuous or categorical. For example, the signal quality indicator may represent the presence, intensity, duration (length of movement), type of movement, and localization of a motion artifact. For example, the signal quality indicators may reflect that a patient lifted a body part. The alarm generator 130 uses the contact pressure data 212, the physiologic data 222, the signal quality indicators, and the current alarm condition status 224 to determine whether to generate an alarm 250.

The data quality detector 110 performs continuous detection of patient movement using pressure-sensitive sensors embedded in object 205. With embodiments, the object 205 may be a mat, a wearable item, a mattress, a bedsheet, a fabric, or similar embodiments; and the pressure-sensitive sensors are embedded in the object 205. With embodiments, the object 205 may be described as a non-contact, non-invasive pressure-sensitive mat technology that may be unobtrusively placed beneath the patient's bedsheet. Alternatively, a patient may lie directly (and be in contact with) the insulated cover of the pressure-sensitive mat. The contact pressure data obtained from the pressure-sensitive sensors may be used to identify periods of patient movement and to generate the signal quality indicators.

Because the pressure-sensitive mat is non-contact, non-invasive and unobtrusive to routine patient care, the pressure-sensitive mat causes no harm to the patient and to staff working with the patient. Other types of object 205, such as pressure-sensitive mattresses or wearable items, also cause no harm to the patient and to staff working with the patient. The physiologic monitor 120 may acquire large volumes of information-rich multi-dimensional physiologic data, including the contact pressure data.

The data quality detector 110 applies sensor fusion between the contact pressure data and the physiologic data to reduce the impact of motion artifacts on physiologic monitor alarms. In particular, the data quality detector 110 uses sensor fusion techniques to detect, mitigate, and suppress motion artifacts to reduce the number of false alarms caused by motion artifacts. Thereby, reducing the false alarm rates on physiologic monitors, alarm fatigue, noise, and staff desensitization. This advantageously improves the data quality and also the quality of care at the patient bedside. Also, with embodiments, the alarm generator 130 is more efficient as it generates fewer alarms overall and/or fewer false-positive alarms.

The data quality detector 110 detects motion artifacts using contact pressure data and fuses that information with physiologic data to reduce false alarm rates on physiologic monitors. Motion artifacts may be patient-initiated or externally-induced during routine care (e.g., diaper changes, feeding, etc.) and during clinical interventions (e.g., nasal gavage tube insertion, endotracheal intubation, etc.).

The data quality detector 110 assesses the quality of data and generates (e.g., triggers or issues) relevant alarms with high specificity and low false alarm rates. When physiologic data indicates an alarm condition, this is first compared to contact pressure data. If there is an indication that the patient may be moving, the alarm is momentarily delayed to see if the alarm condition resolves as the movement decreases. If there is no significant movement (e.g., movement is less than a threshold) or if the alarm condition persists beyond a safety limit, then the alarm generator 130 generates an alarm. The data quality detector 110 safely and significantly reduces false alarms due to movement artifacts.

The data quality detector 110 acquires contact pressure data from the sensors of the object (e.g., a pressure-sensitive mat). The artifact detection unit 240 analyzes the contact pressure data to detect patient movement that is the cause of motion artifacts in physiologic data streams and to generate the signal quality indicators indicating the status of data integrity. Subsequently, the artifact detection unit 240 fuses the contact pressure data and the signal quality indicators with other synchronized physiologic data streams acquired from physiologic monitors routinely attached to the patient (e.g., the electrocardiograph and pulse oximeter). Such sensor fusion results in the detection, mitigation, and suppression of motion artifacts on the physiologic data streams. The alarm generator 130 uses alarm generation techniques to assess the output of the artifact detection unit 240 prior to generating a patient alarm on a given physiologic data stream. Thus, the data quality detector 110 reduces the number of false alarms that are generated primarily due to motion artifacts on physiologic data streams. That is, the data quality detector 110 uses the contact pressure data to assess the quality of the physiologic data to determine whether to issue an alarm for an alarm condition of the physiologic data.

Figure 3:
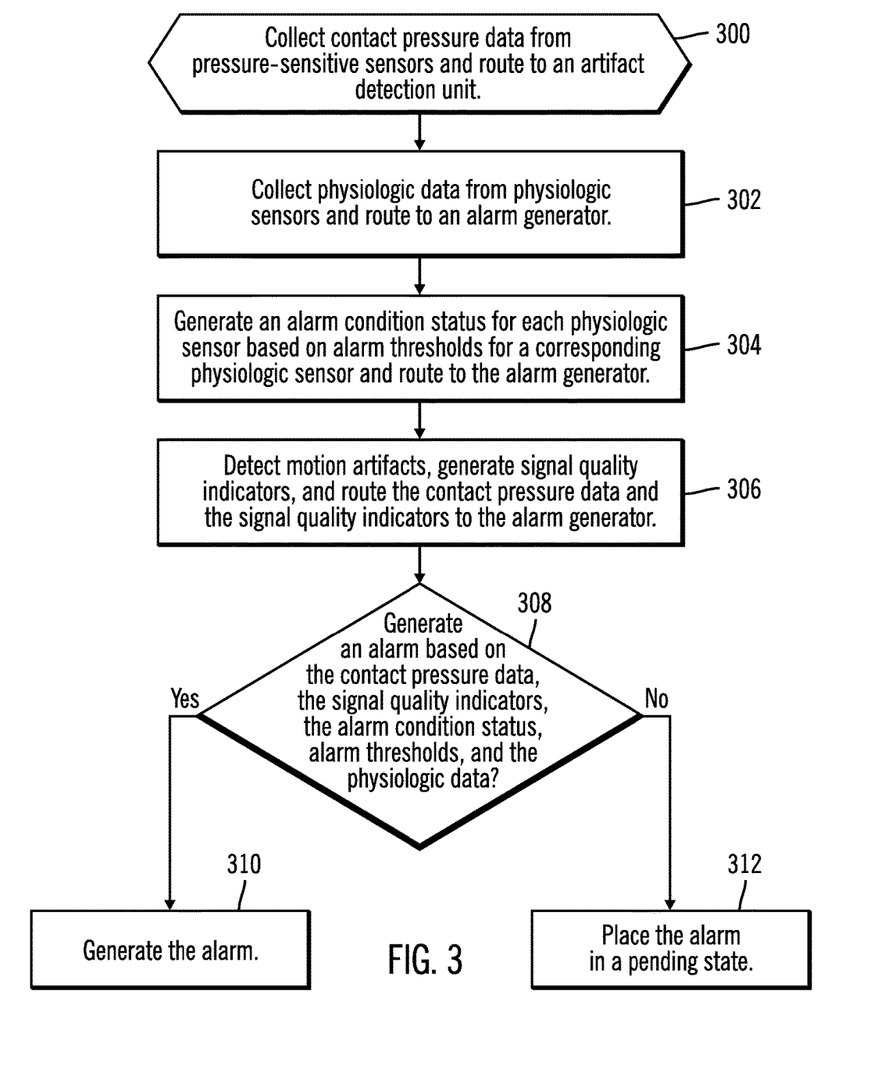
FIG. 3 illustrates, in a flow chart, operations for determining whether to generate an alarm in accordance with certain embodiments.

FIG. 3 illustrates, in a flow chart, operations for determining whether to generate an alarm in accordance with certain embodiments. Control begins at block 300 with the physiologic monitor 120 collecting contact pressure data from pressure-sensitive sensors and routing the contact pressure data to the artifact detection unit 240. With embodiments, an object with pressure-sensitive sensors is placed on the patient's mattress beneath the bedsheet, such that the patient lays on top of the bedsheet and has no direct contact with the object.

In block 302, the physiologic monitor 120 collects physiologic data from physiologic sensors and routes to an alarm generator. In block 304, the physiologic monitor generates an alarm condition status for each physiologic sensor based on alarm thresholds for a corresponding physiologic sensor and routes each alarm condition status and the alarm thresholds to the alarm generator 130.

With embodiments, data from the two sources is recorded simultaneously in each session: (a) contact pressure data from pressure-sensitive sensors and (b) physiologic data and alarm condition status from the physiologic sensors (e.g., the ECG or $SpO_2$ data stream accompanied by its alarm condition status).

In block 306, the artifact detection unit 240 detects motion artifacts from the contact pressure data, generates signal quality indicators, and routes the contact pressure data and signal quality indicators to the alarm generator. In particular, the artifact detection unit 240 uses machine learning techniques called artifact detection techniques to detect motion artifacts generated by patient-related events (including patient movement, routine care, and clinical interventions) by examining the contact pressure data in real-time. These artifact detection techniques shall produce signal quality indicators corresponding to the detected signal quality. The artifact detection techniques are trained using annotations of the patient-related events (including patient movement, routine care, and clinical interventions) during a clinical trial. In certain embodiments, the artifact detection unit 240 receives as inputs the location of the detected movement and the known location of the relevant sensors.

In block 308, the alarm generator 130 determines whether to generate an alarm based on the contact pressure data, the signal quality indicators, the current alarm condition status, alarm thresholds, and the physiologic data. With embodiments, a set of rules are used to determine whether to generate the alarm. With embodiments, each rule is based on any combination of the contact pressure data, the signal quality indicators, the current alarm condition status, alarm thresholds, and the physiologic data. For example, one rule may be: if the contact pressure data shows motion artifacts of a, the signal quality indicators are b, the current alarm condition status is c, alarm thresholds d, and the physiologic data e, then generate alarm, but if the signal quality indicators are z or the physiologic data is x, delay generation of the alarm. With embodiments, if there is an alarm condition in a pending state, but the contact pressure data indicates a concurrent motion artifact and therefore a low signal quality indicator on the alarming data stream, then the alarm generator 130 may consider delaying the alarm. The alarm generator 130 continues to assess the SQI until a maximum delay is reached, and if the alarm condition resolves during the delay period then the alarm condition is cleared, else if the alarm condition reaches the maximum delay period then it is issued regardless. With embodiments, the alarm generator 130 uses alarm generation techniques that consume the signal quality indicators and fuse it with the physiologic data stream, for example, the ECG or $SpO_2$ data stream. These alarm generation techniques may be referred to as sensor fusion techniques. In certain embodiments, the alarm condition indicates that no alarm is needed, and so the alarm is not generated.

Figure 4:
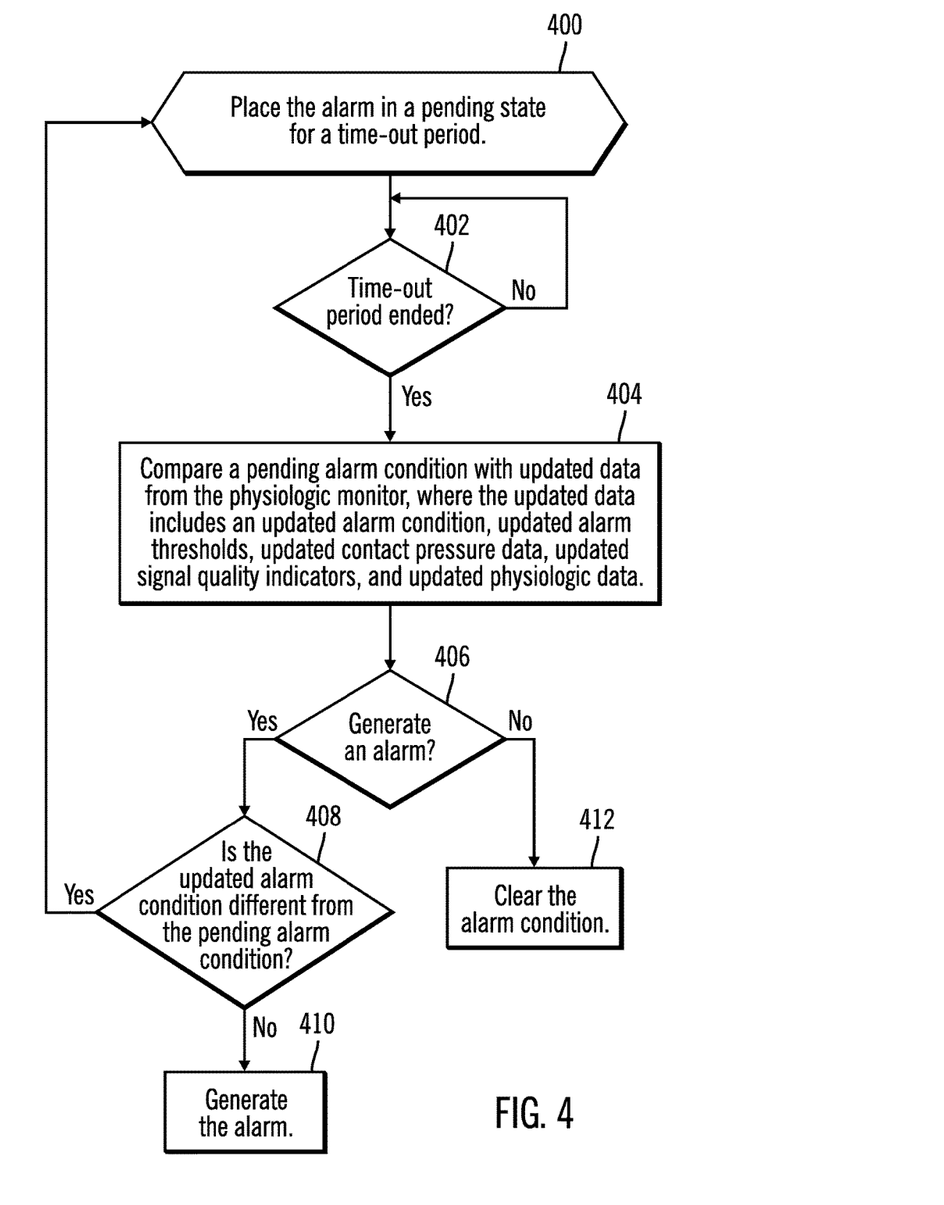
FIG. 4 illustrates, in a flow chart, further details of operations for placing an alarm in a pending state in accordance with certain embodiments.

If the alarm is to be generated, processing continues to block 310, otherwise, processing continues to block 312. In block 310, the alarm generator 130 generates the alarm. In block 312, the alarm generator 130 places the alarm in a pending state and does not generate the alarm. FIG. 4 provides further details of placing the alarm in a pending state.

With embodiments, the alarm may be a sound, a flashing light, a message sent to a computer, etc. The alarm generation techniques may provide a reduced indication of an alarm. For example, a visual indicator that an alarm is pending, but is currently being suppressed due to suspected movement.

For example, if the patient is kicking the left leg, the $SpO_2$ sensor is known to be attached to that limb, and the $SpO_2$ estimate is acting erratically, then the alarm generator 130 determines whether to suppress a pending alarm until the movement ceases and a higher quality $SpO_2$ estimate or signal quality indicators become available.

With embodiments, there is a time-out period, so that a pending alarm is not suppressed indefinitely. With embodiments, once the time-out period for the pending alarm is completed, either the pending alarm is generated or suppressed, but it is no longer pending.

In terms of clinical implementation, physiologic monitors typically have hardware pods or modules for interfacing with specific sensor modalities. For example, one monitor may have modules for interfacing with $SpO_2$ sensors from different vendors. A module may be provided for interfacing with the pressure-sensitive sensors grid.

FIG. 4 illustrates, in a flow chart, further details of operations for placing the alarm in a pending state in accordance with certain embodiments. Control begins at block 400 with the alarm generator 130 placing the alarm in a pending state for a time-out period. In block 402, the alarm generator 130 determines whether the time-period ended. If so, processing continues to block 404, otherwise, processing loops back to block 402. With embodiments, the time-out period may be based on any of a duration of movement and a maximum fixed period of time. Also, there may be different time-out periods for different types and severity of alarms.

In block 404, the alarm generator 130 compares a pending alarm condition with updated data from the physiologic monitor 120, where the updated data includes an updated alarm condition, updated alarm thresholds, updated contact pressure data, updated signal quality indicators, and updated physiologic data.

In block 406, the alarm generator 130 determines whether to generate an alarm. If so, processing continues to block 408, otherwise, processing continues to block 412.

In block 408, the alarm generator 130 determines whether the updated alarm condition is different from the pending alarm condition. If so, processing loops to block 400 (to place the updated alarm condition in a pending state for a time-out period), otherwise, processing continues to block 410. The updated alarm condition may be a new alarm condition. For example, if the current alarm condition indicates that a patient's heartbeat is slower than normal, then the updated (new) alarm condition may indicate that the patient's heartbeat is faster than normal.

In block 410, the alarm generator 130 generates the alarm. With embodiments, generating the alarm also updates the alarm condition from the pending state to an issued state.

In block 412, the alarm generator 130 clears the alarm condition and does not generate the alarm. Clearing the alarm condition may include updating the alarm condition status to indicate that an alarm does not need to be generated. With embodiments, if multiple alarm conditions have been detected, then each of the multiple alarm conditions is cleared.

Figure 5:
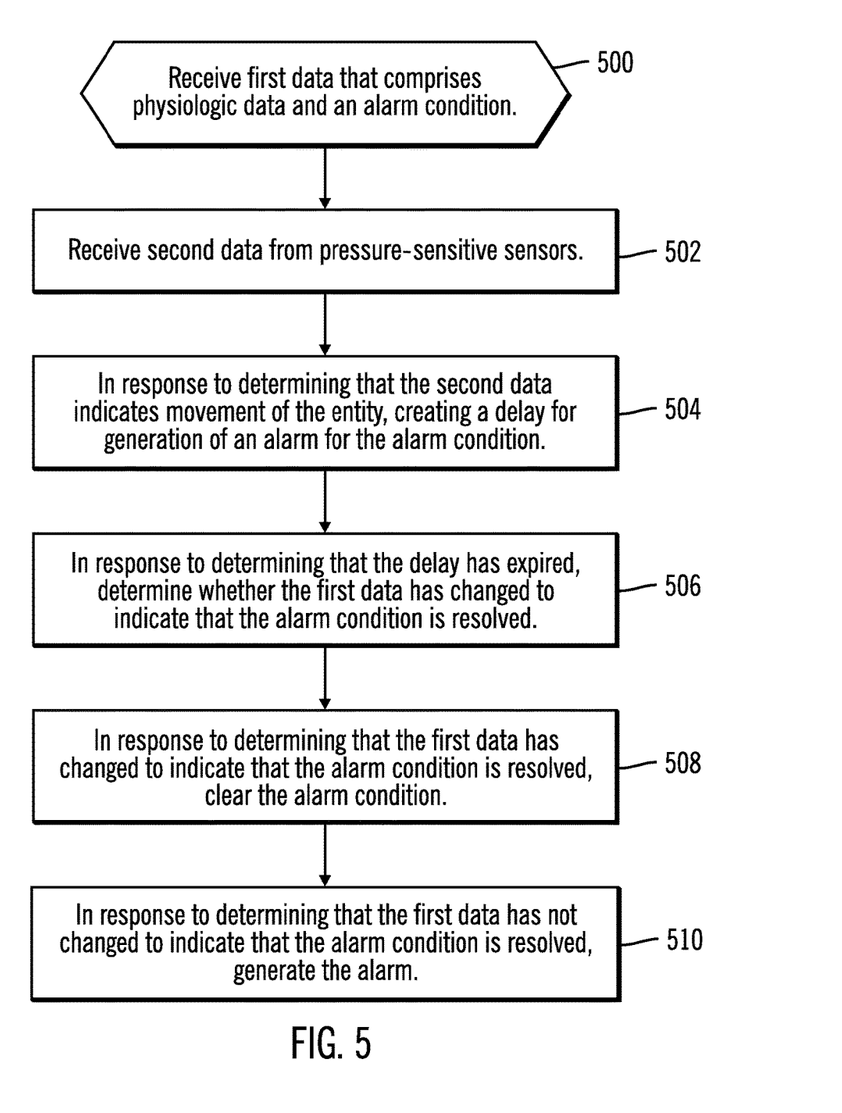
FIG. 5 illustrates, in a flow chart, operations for generating and clearing an alarm condition in accordance with certain embodiments.

FIG. 5 illustrates, in a flow chart, operations for generating and clearing an alarm condition in accordance with certain embodiments. Control begins at block 500 with the data quality detector 110 receiving first data that comprises physiologic data and an alarm condition. In block 502, the data quality detector 110 receives second data from pressure-sensitive sensors. The second data is contact pressure data. In block 504, the data quality detector 110, in response to determining that the second data indicates movement of the entity, creating a delay for generation of an alarm for the alarm condition. In block 506, the data quality detector 110, in response to determining that the delay has expired, determines whether the first data has changed to indicate that the alarm condition is resolved. In block 508, the data quality detector 110, in response to determining that the first data has changed to indicate that the alarm condition is resolved, clearing the alarm condition. In block 510, the data quality detector 110, in response to determining that the first data has not changed to indicate that the alarm condition is resolved, generates the alarm.

With embodiments, the artifact detection unit 240 tracks the location of physiologic monitoring sensors on the body of a patient (e.g., $SpO_2$ sensor that is known to be on left ankle). The location information may be provided by a nurse or other entity. In addition, the artifact detection unit 240 detects patient movements using the pressure-sensitive sensors. Then, the artifact detection unit 240 determines which portions (e.g., limbs, head, torso, etc.) of the body are involved in movement and overall degree of movement. Next, the alarm generator 130 determines the movement is believed to impact sensor location and determines whether to suppress temporarily an alarm for the duration of the movement. For example, the alarm generator 130 may display a visual indicator that an alarm is pending but is currently being suppressed due to suspected movement. For example, if the patient is kicking a left leg, and the $SpO_2$ sensor is known to be attached to the left leg, and the $SpO_2$ estimate is acting erratically, then consider suppressing a pending alarm until the movement ceases and a higher quality $SpO_2$ estimate becomes available.

Embodiments use sensor fusion to combine the movement detection data from the pressure-sensitive sensors with the physiologic monitor data (physiologic data streams and alarms). With embodiments, this sensor fusion occurs in real-time.

With embodiments, the alarm generator 130 receives input from both the pressure-sensitive sensors and the physiologic sensors. With embodiments, the determination of whether to generate an alarm using sensor fusion may be implemented as part of the software embedded in the alarm generator 130.

With embodiments, determining whether to suppress alarms based on detected movements is optimized using actual patient data (i.e., historical data).

Embodiments reduce false alarm rates when monitoring physiologic data. Also, embodiments improve quality of care for a patient by reducing false alarm rates as this avoids the noise and alarm fatigue caused by false alarms.

Embodiments are especially helpful in the NICU and other clinical set ups, including an Intensive Care Unit (ICU), a general ward, a long-term care facility, and home monitoring. Embodiments incorporate data recorded from the pressure-sensitive mat placed underneath a patient (e.g., underneath the crib bedsheet of a neonatal patient). The pressure-sensitive sensors (e.g., of a mat) enable continuously detecting patient movement unobtrusively in a non-contact and non-invasive manner.

Embodiments provide data analysis that examines features derived from contact pressure data, which are indicative of patient-related events (including self-initiated and externally-induced movements) that occur during routine care and clinical interventions. Embodiments identify and suppress motion artifacts in physiologic data streams through sensor fusion. With embodiments, the physiologic data streams include, but are not limited to an $SpO_2$ data stream, a heart rate and/or heart rate variability data stream, and a respiratory rate and/or respiratory rate variability data stream.

Embodiments use the pressure-sensitive sensors as an additive, contactless physiologic monitoring modality in a medical unit to identify patient movement. Embodiments report that movement is a likely cause of false alarms issued by other sensors attached to the patient. Identification and suppression of false alarms leads to false alarm reduction in the medical unit.

Figure 6:
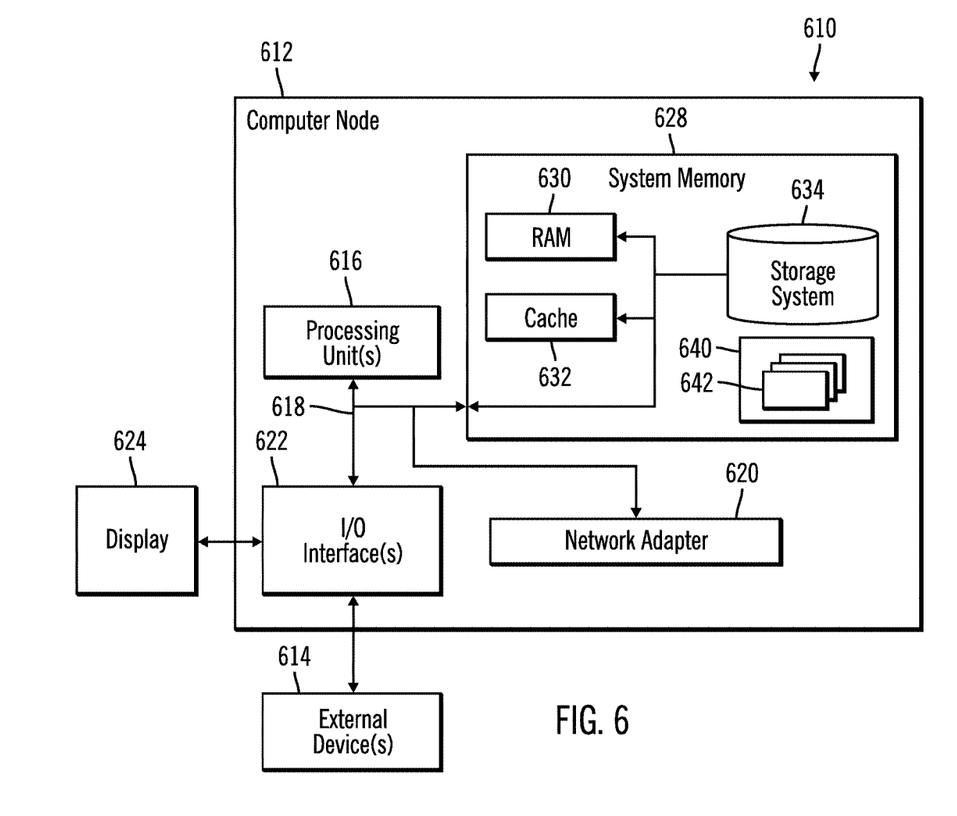
FIG. 6 illustrates a computing node in accordance with certain embodiments.

FIG. 6 illustrates a computing environment 610 in accordance with certain embodiments. In certain embodiments, the computing environment is a cloud computing environment. Referring to FIG. 6, computer node 612 is only one example of a suitable computing node and is not intended to suggest any limitation as to the scope of use or functionality of embodiments of the invention described herein. Regardless, computer node 612 is capable of being implemented and/or performing any of the functionality set forth hereinabove.

The computer node 612 may be a computer system, which is operational with numerous other general purpose or special purpose computing system environments or configurations. Examples of well-known computing systems, environments, and/or configurations that may be suitable for use with computer node 612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer node 612 may be described in the general context of computer system executable instructions, such as program modules, being executed by a computer system. Generally, program modules may include routines, programs, objects, components, logic, data structures, and so on that perform particular tasks or implement particular abstract data types. Computer node 612 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer node 612 is shown in the form of a general-purpose computing device. The components of computer node 612 may include, but are not limited to, one or more processors or processing units 616, a system memory 628, and a bus 618 that couples various system components including system memory 628 to one or more processors or processing units 616.

Bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer node 612 typically includes a variety of computer system readable media. Such media may be any available media that is accessible by computer node 612, and it includes both volatile and non-volatile media, removable and non-removable media.

System memory 628 can include computer system readable media in the form of volatile memory, such as random access memory (RAM) 630 and/or cache memory 632. Computer node 612 may further include other removable/non-removable, volatile/non-volatile computer system storage media. By way of example only, storage system 634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 618 by one or more data media interfaces. As will be further depicted and described below, system memory 628 may include at least one program product having a set (e.g., at least one) of program modules that are configured to carry out the functions of embodiments of the invention.

Program/utility 640, having a set (at least one) of program modules 642, may be stored in system memory 628 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the invention as described herein.

Computer node 612 may also communicate with one or more external devices 614 such as a keyboard, a pointing device, a display 624, etc.; one or more devices that enable a user to interact with computer node 612; and/or any devices (e.g., network card, modem, etc.) that enable computer node 612 to communicate with one or more other computing devices. Such communication can occur via Input/Output (I/O) interfaces 622. Still yet, computer node 612 can communicate with one or more networks such as a local area network (LAN), a general wide area network (WAN), and/or a public network (e.g., the Internet) via network adapter 620. As depicted, network adapter 620 communicates with the other components of computer node 612 via bus 618. It should be understood that although not shown, other hardware and/or software components could be used in conjunction with computer node 612. Examples, include, but are not limited to: microcode, device drivers, redundant processing units, external disk drive arrays, RAID systems, tape drives, and data archival storage systems, etc.

In certain embodiments, the computing device 100 has the architecture of computer node 612. In certain embodiments, the computing device 100 is part of a cloud infrastructure. In certain alternative embodiments, the computing device 100 is not part of a cloud infrastructure.

Cloud Embodiments

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 7:
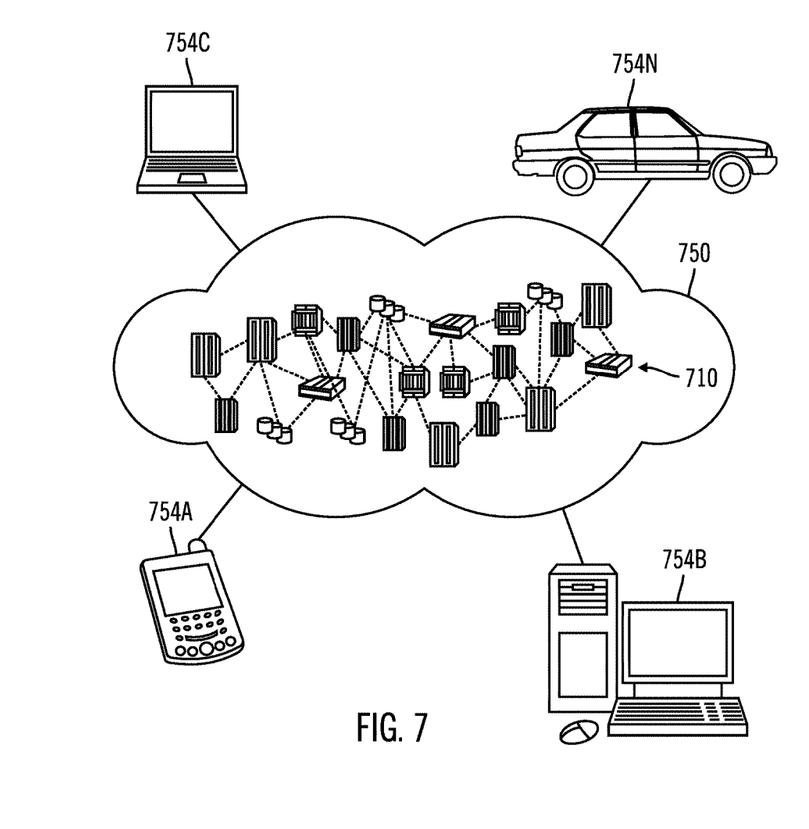
FIG. 7 illustrates a cloud computing environment in accordance with certain embodiments.

Referring now to FIG. 7, illustrative cloud computing environment 750 is depicted. As shown, cloud computing environment 750 includes one or more cloud computing nodes 710 with which local computing devices used by cloud consumers, such as, for example, personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
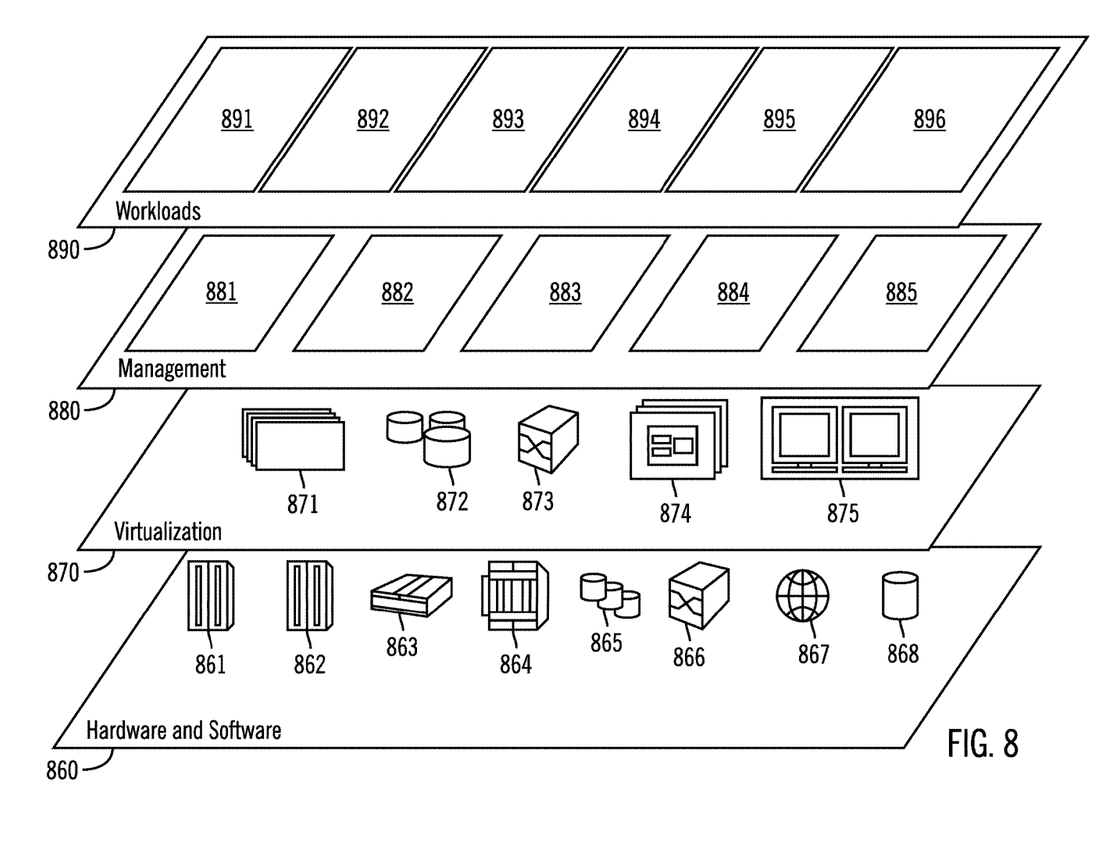
FIG. 8 illustrates abstraction model layers in accordance with certain embodiments.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and detecting quality of physiologic data using contact pressure data for alarm generation 896.

Thus, in certain embodiments, software or a program, implementing detecting quality of physiologic data using contact pressure data for alarm generation in accordance with embodiments described herein, is provided as a service in a cloud environment.

Additional Embodiment Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method, comprising operations of:
    receiving first data that comprises physiologic data and an alarm condition;
    receiving second data from pressure-sensitive sensors, wherein the second data comprises contact pressure data;
    in response to determining that the second data indicates movement of an entity, creating a delay for generation of an alarm for the alarm condition for a time-out period selected based on a type and a severity of the alarm;
    in response to creating the delay for generation of the alarm, displaying a visual indicator that the alarm is pending and is being suppressed due to suspected movement;
    in response to determining that the delay has expired, determining whether the first data has changed to indicate that the alarm condition is resolved;
    in response to determining that the first data has changed to indicate that the alarm condition is resolved, clearing the alarm condition; and
    in response to determining that the first data has not changed to indicate that the alarm condition is resolved, generating the alarm.

2. The method of claim 1, further comprising:
    performing sensor fusion to combine the first data and the second data.

3. The method of claim 1, further comprising:
    determining that there are no motion artifacts impacting the physiologic data; and
    generating the alarm without the delay.

4. The method of claim 1, wherein the first data is collected from sensors connected to the entity, and wherein the second data is collected from the pressure-sensitive sensors connected to an object.

5. The method of claim 1, wherein the time-out period is further based on any of a computed duration and a maximum fixed period of time.

6. The method of claim 1, wherein a Software as a Service (SaaS) is configured to perform the operations of the computer-implemented method.

7. A computer program product, the computer program product comprising a computer readable storage medium having program code embodied therewith, the program code executable by at least one processor to perform operations of:
    receiving first data that comprises physiologic data and an alarm condition;
    receiving second data from pressure-sensitive sensors, wherein the second data comprises contact pressure data;
    in response to determining that the second data indicates movement of an entity, creating a delay for generation of an alarm for the alarm condition for a time-out period selected based on a type and a severity of the alarm;
    in response to creating the delay for generation of the alarm, displaying a visual indicator that the alarm is pending and is being suppressed due to suspected movement;
    in response to determining that the delay has expired, determining whether the first data has changed to indicate that the alarm condition is resolved;
    in response to determining that the first data has changed to indicate that the alarm condition is resolved, clearing the alarm condition; and
    in response to determining that the first data has not changed to indicate that the alarm condition is resolved, generating the alarm.

8. The computer program product of claim 7, wherein the program code is executable by the at least one processor to perform:
    performing sensor fusion to combine the first data and the second data.

9. The computer program product of claim 7, wherein the program code is executable by the at least one processor to perform:
    determining that there are no motion artifacts impacting the physiologic data; and
    generating the alarm without delay.

10. The computer program product of claim 7, wherein the first data is collected from sensors connected to the entity, and wherein the second data is collected from the pressure-sensitive sensors connected to an object.

11. The computer program product of claim 7, wherein the time-out period is further based on any of a computed duration and a maximum fixed period of time.

12. The computer program product of claim 7, wherein a Software as a Service (SaaS) is configured to perform the operations of the computer program product.

13. A computer system, comprising:
    one or more processors, one or more computer-readable memories and one or more computer-readable, tangible storage devices; and
    program instructions, stored on at least one of the one or more computer-readable, tangible storage devices for execution by at least one of the one or more processors via at least one of the one or more memories, to perform operations comprising:

receiving first data that comprises physiologic data and an alarm condition;

receiving second data from pressure-sensitive sensors, wherein the second data comprises contact pressure data;

in response to determining that the second data indicates movement of an entity, creating a delay for generation of an alarm for the alarm condition for a time-out period selected based on a type and a severity of the alarm;

in response to creating the delay for generation of the alarm, displaying a visual indicator that the alarm is pending and is being suppressed due to suspected movement;

in response to determining that the delay has expired, determining whether the first data has changed to indicate that the alarm condition is resolved;

in response to determining that the first data has changed to indicate that the alarm condition is resolved, clearing the alarm condition; and in response to determining that the first data has not changed to indicate that the alarm condition is resolved, generating the alarm.

14. The computer system of claim 13, wherein the operations further comprise:

performing sensor fusion to combine the first data and the second data.

15. The computer system of claim 13, wherein the operations further comprise:

determining that there are no motion artifacts impacting the physiologic data; and generating the alarm without delay.

16. The computer system of claim 13, wherein the first data is collected from sensors connected to the entity, and wherein the second data is collected from the pressure-sensitive sensors connected to an object.

17. The computer system of claim 13, wherein a Software as a Service (SaaS) is configured to perform the operations of the computer system.

18. The computer system of claim 13, wherein the time-out period is further based on any of a computed duration and a maximum fixed period of time.

* * * * *